United States Patent [19]

McMahon

[11] Patent Number: 5,329,820
[45] Date of Patent: Jul. 19, 1994

[54] MATERIALS TESTING GRIP

[75] Inventor: Stephen M. McMahon, Quincy, Mass.

[73] Assignee: Instron Corporation, Canton, Mass.

[21] Appl. No.: 62,701

[22] Filed: May 17, 1993

Related U.S. Application Data

[63] Continuation of Ser. No. 804,284, Dec. 9, 1991, abandoned.

[51] Int. Cl.$^5$ .............................................. G01N 3/08
[52] U.S. Cl. .............................................. 73/833
[58] Field of Search ....................... 73/828, 830–833, 73/856, 858–860; 269/206, 254 R, 275

[56] References Cited

U.S. PATENT DOCUMENTS

| | | | |
|---|---|---|---|
| 544,226 | 8/1895 | Higham | 269/254 R |
| 1,520,716 | 12/1924 | Judd | 73/856 |
| 3,224,259 | 12/1965 | De Nicola | 73/859 |
| 4,292,852 | 10/1981 | Morris | 73/833 |
| 4,579,322 | 4/1986 | Schwarz | 269/275 |
| 5,024,428 | 6/1991 | Ramsay | 209/275 |
| 5,050,437 | 9/1991 | Etter | 73/831 |

FOREIGN PATENT DOCUMENTS 1441239 11/1983 U.S.S.R. .............................. 73/856

Primary Examiner—Robert Raevis

[57] ABSTRACT

A materials testing grip for tensile testing of small fibers includes a pair of inwardly converging surfaces into which a fiber may be easily pressed, and which in fiber tension is characterized by increased gripping force.

8 Claims, 11 Drawing Sheets

MATERIALS TESTING GRIP this is a continuation of application Ser. No. 804,284, filed Dec. 9, 1991, now abandoned.

FIELD OF THE INVENTION

This invention relates to materials testing grips, and more particularly to such grips especially useful in connection with tensile testing of single fiber specimens of very small diameter.

BACKGROUND OF THE INVENTION

Prior art grips used with very small diameter (e.g., 10 to 50 microns) filaments have included grips with flat rubber gripping pad surfaces, such as the pneumatic grips sold by the assignee hereof, Instron Corporation, Canton, Mass., under the designation Model 2712, and the mechanically actuated grips sold by said assignee under the designation Model 2711. Such prior art grips have also included grips in which a fiber is wrapped around a conical "horn" and then pressed thereagainst, as in devices sold by said assignee under the designation Model 2714.

SUMMARY OF THE INVENTION

I have discovered that a grip may be desirably provided by inclusion of surfaces at an angle to each other to permit easy transverse introduction of a specimen therebetween owing to force applied normal (transverse of) to the specimen, with increased frictional resistance to longitudinal movement of the specimen as the specimen moves transversely further into the zone between the surfaces owing to tension thereon longitudinally.

In preferred embodiments, the surfaces are provided by abutting torus-shaped elements, or turns of an element circular in cross-section, held in axial compression.

PREFERRED EMBODIMENTS

Preferred embodiments are shown in the drawings, and described in structure and operation.

DRAWINGS

STRUCTURE

Figures 1, 2:
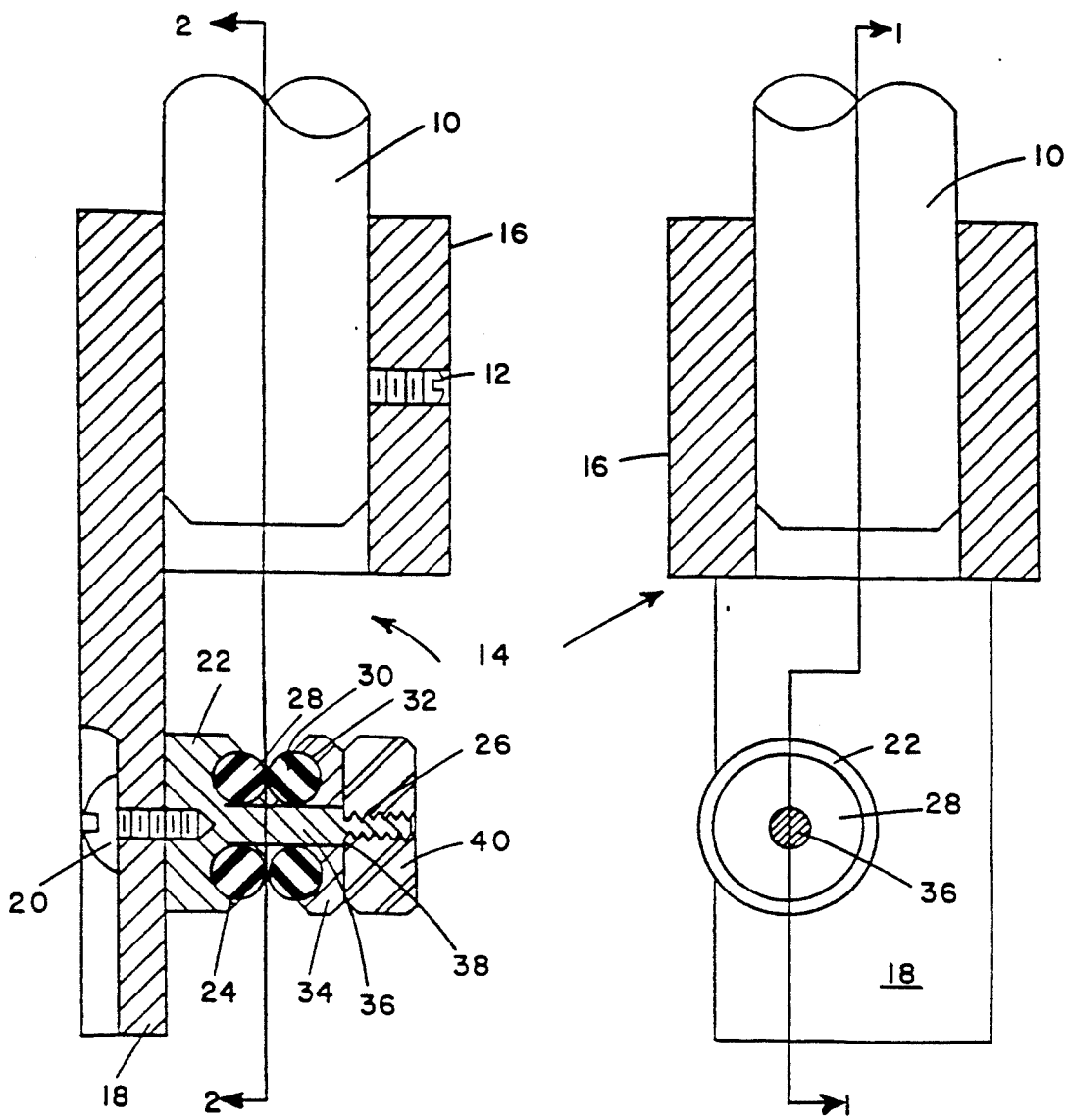
FIG. 1 is a sectional view, taken at 1—1 of FIG. 2, of the presently most preferred embodiment of the invention.
FIG. 2 is a sectional view, taken at 2—2 of FIG. 1, of said embodiment.

There is shown in FIGS. 1 and 2, mounted on mounting rod 10 (which is in turn connected, in a way well known, to an upper load cell, not shown), to which it is secured by set screw 12, a fiber grip indicated generally at 14.

Grip 14 includes an upper annular portion 16 and an integral lower portion 18. Secured to lower portion 18 by screw 20 is jaw support 22, which includes jaw support surface 24 (which is a portion of a torus), and threaded extension 26.

Seated in jaw support surface 24 is elastomeric jaw 28. Elastomeric Jaw 30 is seated in corresponding jaw support surface 32 of second jaw support 34, mounted on stud 36 of jaw support 22, O-ring Jaws 28 and 30 being toral and of the same dimensions and in circular contact therearound.

Threadedly engaged with portion 26 and seated against spindle shoulder 38 is jaws clamp 40.

Grip 14, and its jaws 28, 30, are positioned so that the gripped fiber is coaxial with mounting rod 10 (as well as a corresponding lower mounting rod, not shown), as shown in FIGS. 1 and 2.

The O-rings 28 and 30 are in relaxed form 0.380 inches in outside diameter and 0.250 inches in inside diameter (the hole of the doughnut); the cross-sectional diameter of the annular solid portion is 0.065 inches. When assembled, as shown in FIG. 2, the 0.065 inch diameter is squeezed to 0.040 inches, the cross-section going thus to (as only diagrammatically shown in FIG. 1) an out-of-round one.

O-rings 28 and 30 are formed of a 70-durometer butadiene acrylonitrile polymer (also known as nitrile and Buna-N), sold for example by Nor Rubber Co. Inc., Bloomfield, N.J.

OPERATION

A fiber specimen is loaded into top grip 14 by holding the fiber length between two human hands and pushing it into the V-groove between jaws 28 and 30, following which the top end of the fiber (not shown) is given a half turn around that V-groove, with hand force pressing the half turn into the groove. The lower end of the fiber is then loaded into a bottom grip (not shown, but identical with the top grip, although oppositely oriented, as is the custom in the art with grips generally) in the same way, pushing the lower end of the fiber specimen into the side of that grip's V in line with the axis of mounting rod 10 and the place thereunder coaxial therewith where the fiber is initially gripped in the upper grip 14, and similarly taking and pressing in a half turn of fiber.

The grips are then moved away from each other, in the manner familiar in the art of tensile testing. This movement imposes further forces on the fiber driving it inwardly of the two V's, and providing even tighter gripping, in both grips.

The present invention provides a number of advantages. Loading of very small fibers into the grips is easy. The stationary V-groove nature of them makes repeatability of alignment and position highly repeatable from test to test, especially desirable in use with optical extensometers. Light weight of grips of the invention (e.g., 20 grams) facilitates use of low capacity load cells. All required for loading is to place a fiber in the V; the gradual increased frictional grip as longitudinal pulling proceeds reduces pinching and breaks at the grip. Broken specimens can easily be removed by unwinding from the groove. Actuators are not needed and parts are few and simple, reducing expense (of both manufacture and maintenance), as does the use as Jaws of inexpensive O-rings. Coaxiality of mounting rods and gripped fiber desirably reduce off-center loading effects.

If desired, as may in particular be so with very elastic fibers, in order to improve gripping ability, a fiber may be wound around the grip between-the-jaws V.

OTHER EMBODIMENTS

The jaws may be, instead of a pair of O-rings, a unitary elastomeric Jaw unit with two integral jaw portions divided by a V-groove. Or, they may be two or more turns of a helically wound elastomeric rod. Or, one jaw, or both jaws, may be non-elastomeric. Jaw portions need not completely intersect at the bottom of the zone of angled relationship to define a nip within the invention. The V-groove need not have planar jaw portions, nor need the jaw portions be symmetrical about a plane.

Other embodiments of the invention will occur to those skilled in the art.

What is claimed is:

1. A testing grip combination comprising:
    an actuator element that is movable along an axis,
    a connecting member connected to said actuator element for movement along said axis,
    a first jaw portion attached to said connecting member,
    a second jaw portion, and
    means for limiting movement of said first jaw portion and said second jaw portion thereapart,
    each of said first jaw portion and said second jaw portion having a gripping face,
    each said gripping face facing the other said gripping face,
    the first jaw portion gripping face being out of parallel with the second jaw portion gripping face, and defining therewith a nip that has a portion oriented parallel to said axis so as to receive a test fiber by movement transverse to said axis.

2. The grip combination of claim 1 in which at least one of said gripping faces is a surface of an element of elastomeric material.

3. The grip combination of claim 2 in which at least one of said jaw portions is an elastomeric O-ring.

4. The grip combination of claim 3 in which each of said jaw portions is an elastomeric O-ring, said element of elastomeric material being one of said elastomeric O-rings.

5. The grip combination of claim 4 wherein said means for limiting includes jaw supports in which respective said O-rings are supported.

6. The grip combination of claim 5 in which one said jaw support includes a stud extending through the other said jaw support.

7. The grip combination of claim 6 in which said stud carries threads which engage a nut to urge said jaw supports together to compress said jaw portions.

8. The grip combination of claim 1 in which said jaw portions are portions of an integral helical elastomeric rod.

* * * * *